(12) United States Patent
Palin et al.

(10) Patent No.: US 7,879,612 B2
(45) Date of Patent: Feb. 1, 2011

(54) ORGANIC NON-SUGAR COMPOUNDS FOR PROTECTION OF BIOLOGICALLY ACTIVE MOLECULES AND CONJUGATE LABELS AND METHODS OF USE THEREOF

(76) Inventors: William J. Palin, 32 Olde Fort Rd., Cape Elizabeth, ME (US) 04107; Alan H. Davis, Point of Care Diagnostics, 10 Southgate Rd., Scarborough, ME (US) 04074; Roger N. Piasio, c/o Binax, Inc., 10 Southgate Rd., Scarborough, ME (US) 04074; Erik R. Piasio, 233 Foreside Rd., Cumberland Foreside, ME (US) 04110; Bruce C. Reinemann, 1353 N. Union Rd., Union, ME (US) 04862

( * ) Notice: Subject to any disclaimer, the term of this patent is extended or adjusted under 35 U.S.C. 154(b) by 398 days.

(21) Appl. No.: 11/965,419

(22) Filed: Dec. 27, 2007

(65) Prior Publication Data
US 2008/0248594 A1 Oct. 9, 2008

Related U.S. Application Data

(63) Continuation of application No. PCT/US2006/024955, filed on Jun. 27, 2006.

(60) Provisional application No. 60/694,604, filed on Jun. 27, 2005.

(51) Int. Cl.
*G01N 33/558* (2006.01)
*G01N 31/00* (2006.01)
(52) U.S. Cl. .............................. 436/8; 422/56; 422/57; 435/4; 435/805; 435/970; 436/18; 436/512; 436/514; 436/810
(58) Field of Classification Search .................... None
See application file for complete search history.

(56) References Cited

U.S. PATENT DOCUMENTS 7,285,426 B2 * 10/2007 Bohannon et al. ............ 436/514
7,319,032 B2 * 1/2008 Bohannon et al. ......... 435/287.2

* cited by examiner

*Primary Examiner*—Christopher L Chin
(74) *Attorney, Agent, or Firm*—Foley Hoag LLP

(57) ABSTRACT

Provided are methods comprising the use of non-sugar organic compatible solutes for protection and preservation of the activity of biologically active molecules and conjugate labels. The methods are particularly adaptable for use in conjunction with immunoassays, such as for example, immunochromatographic test assays and may be incorporated into any test methodology wherein a dry test strip is used as a carrier for depositing, mobilizeable and/or immobilized biologically active molecules and/or conjugate labels.

17 Claims, 2 Drawing Sheets

The Malaria Urine Dipstick ICT

4°C Conjugate Pad Control

Conjugate Pad 19mo at 55°C

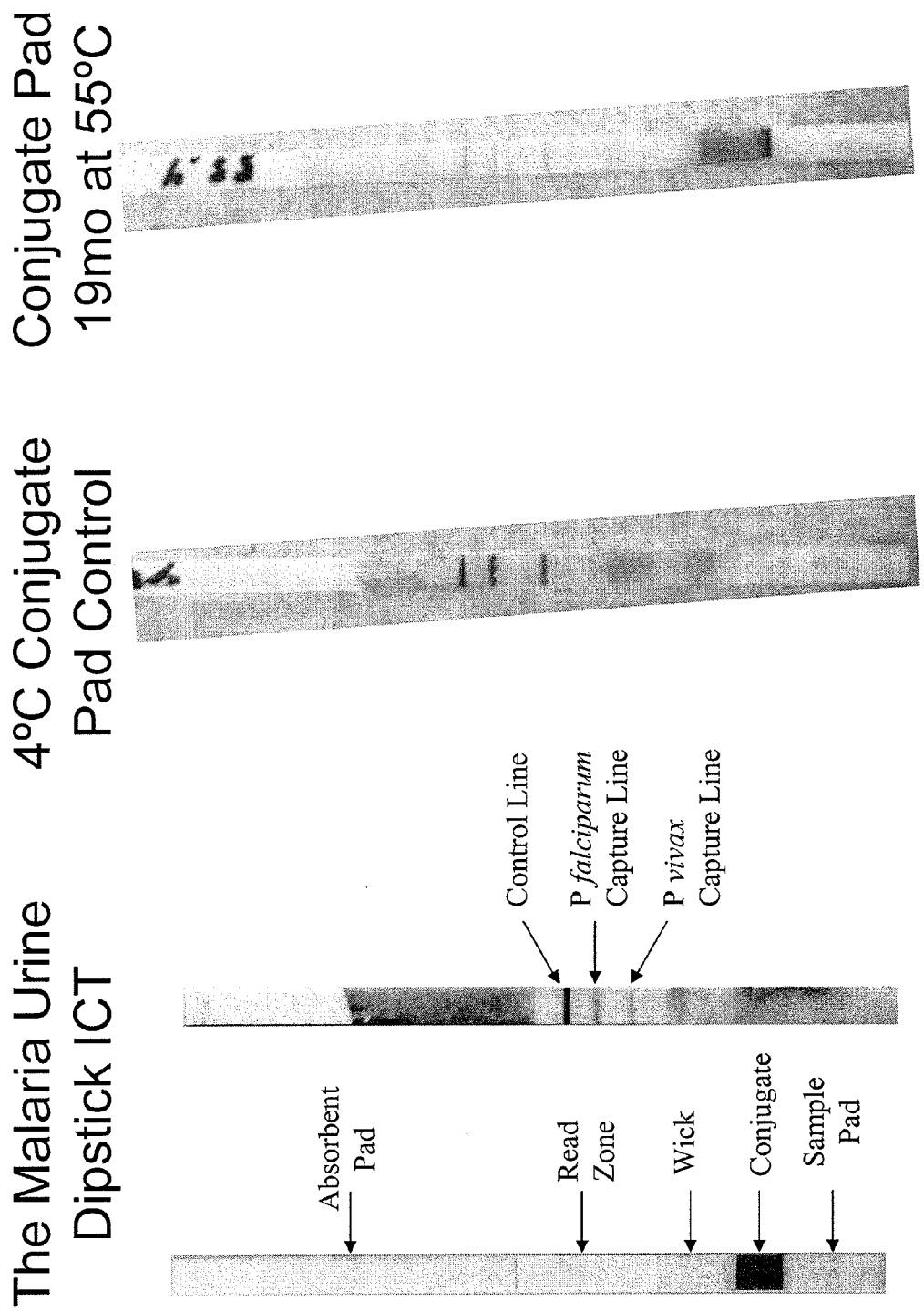

US 7,879,612 B2

ORGANIC NON-SUGAR COMPOUNDS FOR PROTECTION OF BIOLOGICALLY ACTIVE MOLECULES AND CONJUGATE LABELS AND METHODS OF USE THEREOF

RELATED APPLICATIONS

This application is a continuation of PCT/US2006/024955 filed Jun. 27, 2006, which claims priority to U.S. Provisional Patent Application 60/694,604, filed Jun. 27, 2005, which applications are hereby incorporated by reference in their entirety.

BACKGROUND OF THE INVENTION

A variety of buffers and stabilizers for use in conjunction with proteins are commercially available. These solvents and buffers can be used in a variety of procedures and tests including immunoassays. Many of the available buffers and stabilizers become ineffective in protecting and preserving the activity of biologically active molecules and conjugate labels under the dry conditions of immunochromatographic test assays. Some immunochromatographic test assays have a very short shelf-life and oftentimes lose effectiveness or become totally ineffective in a short period of time due to the degradation of the activity of the molecules during storage in dry conditions. While there has been a trend to produce more effective and longer lasting immunochromatographic test assays, further improvements for effectiveness and preservation of activity of active molecules and conjugate labels are desirable.

SUMMARY OF THE INVENTION

Provided are methods of using non-sugar organic compatible solutes for protection and preservation of the activity of biologically active molecules and conjugate labels. We have found that the activity of biologically active molecules deposited on dry carriers of immunochromatographic test (ICT) assays can be preserved, protected and kept preserved for longer durations of time when deposited together with one or more non-sugar organic compatible solutes. Non-sugar organic compatible solutes may be used in conjunction with immunoassays, such as for example ICT assays, but also in any application wherein the protection and preservation of the activity of biologically active molecules and conjugate labels is desired, for example, in solution phase, in dry state, or in reconstituted state. The non-sugar organic compatible solutes may be combined with any test methodology wherein a dry test strip is used as a carrier for depositing mobilizable and/or immobilized biologically active molecules and/or conjugate labels.

DESCRIPTION OF THE DRAWINGS

FIG. 2 illustrates that 4% w/v of L-Histidine alone does not confer stability to conjugate pad drying buffer without sucrose for a malaria ICT device.

DETAILED DESCRIPTION OF THE INVENTION

1. Introduction

Figure 1:
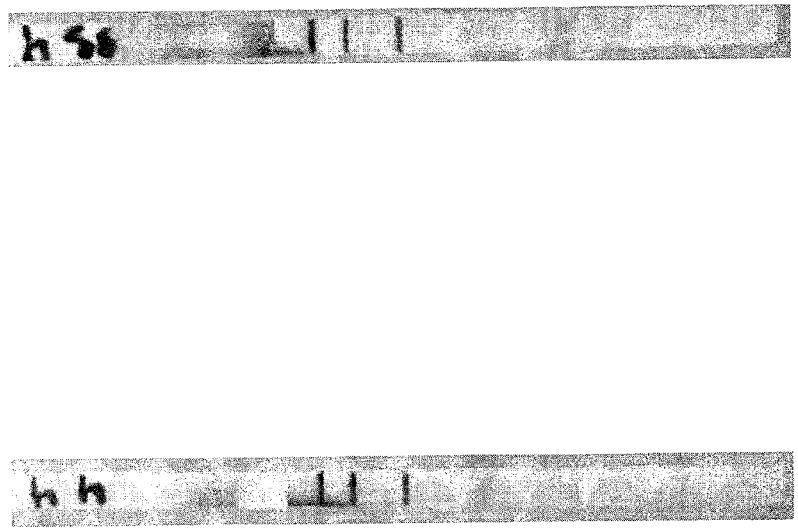
FIG. 1 depicts the stabilizing effect that a combination of 2% w/v of ecotine, L-histidine, taurine and L-threonine has on conjugate pad drying buffer without sucrose for a malaria ICT device. Equivalent sensitivity was observed for conjugate pad stored at both 4° C. and 55° C. despite the absence of sucrose in the drying pad buffer formulation.
Figure 1:
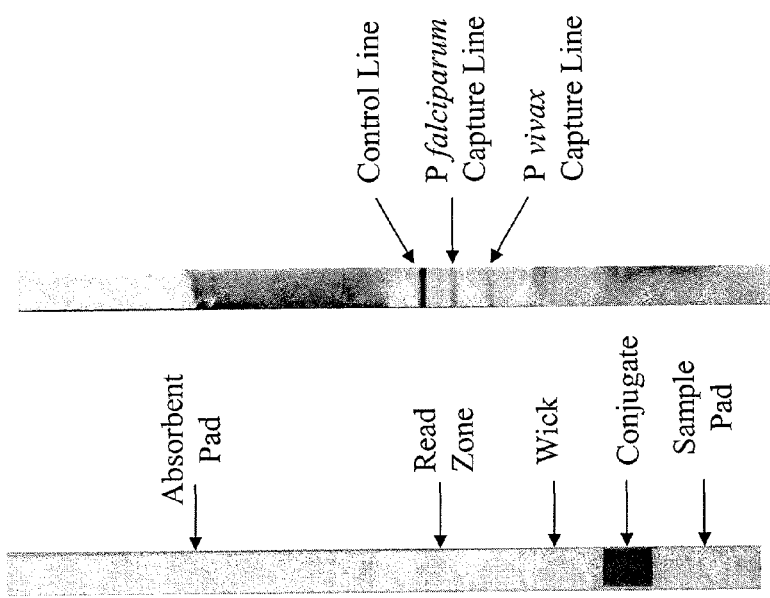

The activity of biologically active molecules can generally be preserved, protected, and kept preserved for longer durations of time when deposited together with one or more non-sugar organic compatible solutes, particularly when deposited on dry carriers of immunochromatographic test assays.

In one aspect, provided is a method comprising:
a) depositing one or more biologically active molecules onto a surface;
b) depositing one or more non-sugar organic compatible solutes onto the surface; and
c) drying the deposited one or more biologically active molecules and the deposited one or more non-sugar organic compatible solutes on the surface; wherein the one or more non-sugar organic compatible solutes protects and preserves the activity of the one or more biologically active molecules in the dried and reconstituted state.

In another aspect, provided is a method comprising:
a) providing a sample;
b) providing a test strip with at least a portion comprising one or more biologically active molecules and one or more non-sugar organic compatible solutes, wherein the one or more non-sugar organic compatible solutes protects and preserves the activity of the one or more biologically active molecules in the dried and reconstituted state.
c) contacting the sample with the test strip; and
d) detecting the presence of or measuring the amount of an analyte of interest in the sample.

In another aspect, provided is a method comprising:
a) providing one or more biologically active molecules; and
b) providing one or more non-sugar organic compatible solutes; wherein the one or more non-sugar organic compatible solutes preserves the activity of the one or more biologically active molecules.

Further objectives and advantages of the present invention will become apparent as the description proceeds. To gain a full appreciation of the scope of the present invention, it will be further recognized that various aspects of the present invention can be combined to make desirable embodiments of the invention.

Unless defined otherwise, all technical and scientific terms used herein have the same meaning as commonly understood by one of ordinary skill in the art to which this invention belongs. Where a term is provided in the singular, the inventor also contemplates the plural of that term. The nomenclature used herein and the procedures described below are those well known and commonly employed in the art.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. The names of the natural amino acids are abbreviated herein in accordance with the recommendations of IUPAC-IUB.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "biologically active molecule" refers to any active organic molecule that is part of a living organism, which may be natural, synthetic, or a combination thereof.

The terms "comprise" and "comprising" is used in the inclusive, open sense, meaning that additional elements may be included.

The term "including" is used herein to mean "including but not limited to". "Including" and "including but not limited to" are used interchangeably.

The terms "label" or "labeled" refer to incorporation or attachment, optionally covalently or non-covalently, of a detectable marker into a molecule, such as a polypeptide, e.g., an antibody. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "test strip" refers to a chromatographic-like medium upon which an assay may be performed.

The term "sample" refers to any fluid sample potentially containing an analyte.

2. Methods for Preserving Activity of Biologically Active Molecules in the Dried and Reconstituted State Provided is the use of non-sugar organic compatible solutes for protection and preservation of the activity of biologically active molecules and conjugate labels. The methods described below are adaptable for use with an immunochromatographic test strip having a porous carrier such as a nitrocellulose test strip, which is well-known in the art.

Provided is a method for preserving the activity of biologically active molecules in the dried and reconstituted state comprising depositing one or more biologically active molecules onto a surface. The one or more biologically active molecules can be deposited onto the surface using any suitable method. The one or more biologically active molecules can be any suitable biologically active molecule, such as, for example, a biologically active molecule that is capable of specifically binding one or more analytes of interest. Suitable molecules of the present invention include, for example, polyclonal or monoclonal antibodies or antibody fragments. The surface can be any type of surface suitable for performing immunoassays, such as, for example, a nitrocellulose test strip.

In certain embodiments, the surface or test strip is part of a lateral flow device. In a lateral flow device, a sample containing a target analyte of interest is added to an application well in the lateral flow device. The test sample flows along a test strip or surface toward a zone containing a mobilizable binding reagent disposed in the zone in a dry state, e.g., in a pad. When the sample front reaches this zone, the mobilizable labeled binding reagent is released from the pad and then allowed to interact with target analyte that may be present in the test sample. Target analyte in the sample binds to the mobilizable binding agent and flow continues toward a detection zone. The detection zone comprises an immobilized unlabelled specific binding reagent, for example, on a pad, for binding to the analyte/mobilizable binding agent complexes. The presence of analyte in the sample is determined by observing the extent (if any) to which the labeled binding agent/analyte complex becomes bound in the detection zone. Results can be assessed visually by colorometric means with the intensity of color being directly proportional to target analyte concentration within the test sample. In one embodiment, the labeled reagent, the analyte (if present) and the immobilized unlabelled specific binding agent cooperate together in a "sandwich" reaction. This results in the labeled reagent being bound in the detection zone if analyte is present in the sample. The two binding reagents must have specificities for different epitopes on the analyte.

An exemplary lateral flow device of this type is disclosed in Davis, et al., U.S. Pat. No. 6,352,862, which is incorporated by reference herein in its entirety.

The method may also comprise depositing one or more non-sugar organic compatible solutes onto a surface. The deposition of the one or more biologically active molecules and the one or more non-sugar organic compatible solutes onto the surface of a carrier or surface can be done in any suitable manner such as concurrent or separate deposition. The one or more non-sugar organic compatible solutes of the present invention can be any non-sugar organic compatible solutes suitable for the purpose of the invention, namely, effective to preserve, and protect, the activity of the one or more biologically active molecules for a longer duration of time than would be possible without the presence of the one or more non-sugar organic compatible solutes. The one or more non-sugar organic compatible solutes of the present invention include, for example, amino acids such as glycine, alanine, serine, proline, sodium glutamate, lysine, aminobutric acid, taurine, amines such as betaine, sarcosine, trimethylamine N-oxide, or osmolytes or other compatible solutes such as 2-naphthol, ectoine, hydroxyectoine, glycerine, deoxyribonucleic acid, adenosine monophosphate, PCR primers, spermine, spermidine, Brij58, polyethyleneimine, polyhystidine, polythymadilic acid, acetyl-L-carnitine, L-carline, hypotaurine, and ferulic acid.

The methods may also comprise drying the deposited one or more biologically active molecules and the deposited one or more non-sugar organic compatible solutes on a surface. Any suitable drying methodology known in the art may be used for drying the deposited one or more biologically active molecules and the one or more non-sugar organic compatible solutes.

An important aspect of the methods is the ability of the one or more non-sugar organic compatible solutes to protect and preserve the activity of the one or more biologically active molecules in the dried and reconstituted state.

3. Methods for Detecting the Presence of or Measuring the Amount of an Analyte of Interest in a Sample Further provided is the use of non-sugar organic compatible solutes for protection and preservation of the activity of biologically active molecules and conjugate labels and methods thereof. The methods provided herein are adaptable for use with an immunochromatographic test strip having a porous carrier such as a nitrocellulose test strip, for example, a lateral flow device, which are numerous and vary in techniques and are well known in the art as described in detail in the previous section.

By way of example, generally, an immunoassay device for determining the presence or amount of an analyte of interest in a sample includes a sample application member, which is in liquid communication with a conjugate pad, which is in liquid communication with a nitrocellulose test strip having a test result zone and a control zone. The immunoassay can also include a distal sink at the end opposite to the sample application pad to absorb any excess liquid after testing has run to completion.

The sample application pad is a porous pad able to absorb the sample to be tested and transfer the absorbed sample to the conjugate pad by capillary action. The conjugate pad includes one or more dried labeled molecules or reagents, such as antibodies, capable of specifically binding to the one or more analytes of interest forming a analyte-labeled reagent complex. The conjugate pad may also include one or more stabilizing compounds that are able to induce thermal stability and also stability as to conditions imposed by humidity and temperature. The conjugate pad is a porous pad able to absorb the transferred sample from the sample application pad and transfer the sample to the nitrocellulose strip by capillary action. The nitrocellulose strip is able to absorb the sample from the conjugate pad and transfer the sample by capillary action downstream to the test result zone and the control zone. The test result zone of the immunoassay device includes one or more immobilized molecules or reagents, such as antibodies, capable of specifically binding to the one or more analytes of interest or any portion of the analyte-labeled reagent complex. The control zone of the immunoassay device may include one or more immobilized molecules or reagents, such as antibodies, capable of specifically binding to the one or more labeled reagent.

When a liquid test sample is applied to the sample application pad of the device, the sample travels through the sample application pad, the conjugate pad, and nitrocellulose strip by capillary action. When the sample travels through the conjugate pad, the sample solublizes the dried labeled molecule or reagent, and if the analyte of interest is present in the sample, the solubilized labeled molecule or reagent binds the analyte of interest forming an analyte-labeled reagent complex, otherwise, if the analyte of interest is not present in the sample, no complex is formed. The analyte-labeled reagent complex in the case of a positive test, or the labeled reagent alone in the case of a negative test, then travel to the nitrocellulose strip and travel through and pass the test result zone and the control zone of the device. If the analyte of interest is present in the sample, the analyte-labeled reagent complex binds to the immobilized reagent of the test result zone forming a detectable line, and if the analyte of interest is not present in the sample, no analyte labeled reagent complex is formed and therefore no binding occurs at the test result zone.

Whether or not the analyte of interest is present in the sample to form a complex, the labeled reagent binds to the immobilized reagent of the control zone forming a detectable line indicating that the test has run to completion. Any excess liquid sample, after the testing has run to completion, can be absorbed at the distal sink of the accused device.

Provided is a method of detecting the presence of or measuring the amount of an analyte of interest in sample including the steps of providing a sample suspected of containing an analyte of interest. The sample can be any sample, such as for example, biological fluids or environmental samples. The method may also include providing a immunochromatographic test strip comprising one or more biologically active molecules and one or more non-sugar organic compatible solutes.

The immunochromatographic test strip is preferably associated with an immunoassay like the devices described above for detecting the presence of or measuring the amount of an analyte of interest in a sample. The method of the present invention also includes the step of contacting the sample suspected of containing the analyte of interest with the immunochromatographic test strip.

The method may also include detecting the presence of or measuring the amount of the analyte of interest The detection of the presence or measurement of the amount of analyte of interest can be done by any suitable method for that purpose, such as for example, use of labeled antibodies or antibody fragments wherein the label includes one or more of, for example, latex, dye, gold sols, radioactive, or fluorescent labels.

An important aspect of the present invention includes the ability of the one or more non-sugar organic compatible solutes to protect and preserve the activity of the one or more biologically active molecules in the dried and reconstituted state, e.g. particularly in a conjugate pad or other zone comprising a mobilizable, dried binding agent, but also binding agents in a detection zone of any of the above-described devices. The one or more non-sugar organic compatible solutes of the present invention may be selected from, for example, amino acids such as glycine, alanine, serine, proline, sodium glutamate, lysine, aminobutric acid, taurine, amines such as betaine, sarcosine, trimethylamine N-oxide, or osmolytes or other compatible solutes such as 2-naphthol, ectoine, hydroxyectoine, glycerine, deoxyribonucleic acid, adenosine monophosphate, PCR primers, spermine, spermidine, Brij5 8, polyethyleneimine, polyhystidine, polythymadilic acid, acetyl-L-carnitine, L-citruline, hypotaurine, and ferulic acid.

EXAMPLES

The invention, having been generally described, may be more readily understood by reference to the following examples, which are included merely for purposes of illustration of certain aspects and embodiments of the present invention, and are not intended to limit the invention in any way. All headings are for the convenience of the reader and should not be used to limit the meaning of the text that follows the heading, unless so specified.

Example 1

RSC Capture

According to this example, ICT devices for the detection of RSV antigens were constructed and used. Capture antibody solutions containing monoclonal anti-RSV (Binax Inc., Portland Me.) at 1.0 mg/mL and 8% (w/v) Taurine (Sigma, St Louis, Mo.) (protected) or monoclonal anti-RSV (Binax Inc., Portland Me.) at 1.0 mg/mL alone (unprotected) were striped immediately after preparation. The capture solutions were striped onto nitrocellulose (HF11 OUBBS, Millipore, Bedford, Mass.) material laminated to a polyester film and dried for two minutes at 48° C. The devices were then built according to the general design of the device using gold labeled anti-RSV. A subset of the finished devices was analyzed the following day (time zero) and the remainder were sealed in foil pouches and stored at 55° C.

Positive (sensitivity, low and moderate) and negative samples for the RSV antibody were applied to the extraction pad of the devices and after 15 minutes they were analyzed for detection of the RSV antigens. Initial testing resulted in a similar response to the positive controls for both the unstabilized and stabilized striped capture solutions. In all cases the negative control did not generate a positive signal. After one week at 55° C. the unprotected devices failed to detect the sensitivity control. By three weeks the low control produced only faint signal for the unprotected devices, while the protected devices generated a response nearly equivalent to that of the protected devices run at week one. Lastly, after two months the unprotected devices were all but unresponsive to the three positive controls. The protected devices continued to detect the RSV antigen in the low and moderate controls.

Example 2

*Streptococcus Pneumoniae* Capture

According to this example, ICT devices for the detection of *S. pneumoniae* antigens were constructed and used. Capture antibody solutions containing affinity purified rabbit anti-*Strep pneumoniae* antibody (Binax Inc, Portland Me.) at 1.25 mg/ml and 5% (w/v) Hydroxyectoine (Fluka Production, GmbH) (protected) or affinity purified rabbit anti-*Strep pneumoniae* antibody (Binax Inc, Portland Me.) at 1.25 mg/ml alone (unprotected) were striped immediately after preparation. The capture solutions were striped onto nitrocellulose (SR, Millipore, Bedford, Mass.) material laminated to a polyester film and dried for two minutes at 50° C. The devices were then built according to the general design of the device using gold labeled rabbit anti-*Strep pneumoniae* antibody. A subset of the finished devices was analyzed the following day (time zero) and the remainder were sealed in foil pouches and stored at 55° C.

Positive (sensitivity low and moderate) and negative samples for the *Strep pneumoniae* antibody were applied to the patient swab in the device followed by the addition of the chase solution and after 15 minutes they were analyzed for detection of the *Strep pneumoniae* antigens. In all cases the negative control did not generate a positive signal. After one week at 55° C. the unprotected devices generated signals half that of the devices stabilized with hydroxyectoine. After one month the low control was not detectable with unprotected devices, while the protected devices continued to detect the sensitivity control. After two months the results were similar to that of the one month time point.

Example 3

Filariasis Capture

According to this example, ICT devices for the detection of RSV antigens were constructed and used. Capture antibody solutions containing monoclonal anti-*D. immitis* IgM (Binax Inc, Portland Me.) at 1.5 mg/d and 5% (w/v) Spermine (Fluka Production, GmbH) (protected) or monoclonal anti-*D. immitis* IgM (Binax Inc, Portland Me.) at 1.5 mg/ml alone (unprotected) were striped immediately after preparation. The capture solutions were striped onto nitrocellulose (HF1 1OUBBS, Millipore, Bedford, Mass.) material laminated to a polyester film and dried for two minutes at 50° C. The devices were then built according to the general design of the device using gold labeled anti-*D. immitis*. A subset of the finished devices was analyzed shortly thereafter (time zero) and the remainder were sealed in foil pouches and stored at 55° C.

Positive (low and moderate) sera and negative whole blood samples for the *D. immitis* antibody were applied to the extraction pad of the devices and after 15 minutes they were analyzed for detection of the *D. immitis* antigens. Initial testing resulted in a similar response to the positive controls for both the unstabilized and stabilized striped capture solutions. In all cases the negative control did not generate a positive signal. After one week at 55° C. the unprotected devices failed to detect the low control while the stabilized devices produced a signal equivalent to the initial testing. After one month the unprotected devices did not detect either the low or the moderate positive control, while the protected devices detected both the low and moderate positive control. After two months the unprotected devices continued to be unresponsive to the positive controls. The protected devices detected the *D. immitis* antigen in the moderate control.

Example 4

RSV Capture

According to this example, ICT devices for the detection of RSV antigens were constructed and used. Capture antibody solutions containing monoclonal anti-RSV (Binax Inc, Portland Me.) at 1.0 mg/mL and 1.25% (w/v) Adenosine S' monophosphate (Sigma, St Louis, Mo.) (protected) was striped immediately after preparation. The capture solution was striped onto nitrocellulose (HFI 1OUBBS, Millipore, Bedford, Mass.) material laminated to a polyester film and dried for two minutes at 48° C. The devices were then built according to the general design of the device using gold labeled anti-RSV. A subset of the finished devices was analyzed the following day (time zero) and the remainder were sealed in foil pouches and stored at 55° C.

Positive (sensitivity, low and moderate) and negative samples for the RSV antibody were applied to the extraction pad of the devices and after 15 minutes they were analyzed for detection of the RSV antigens. Initial testing of the devices with the stabilized RSV antibody detected the RSV antigen in each of the three positive controls, sensitivity, low and moderate. In all cases the negative control did not generate a positive signal. After one week at 55° C. the signal generated by each of the control type was the same as that of the initial testing. The devices continued to detect the RSV antigen in the sensitivity, low and moderate controls after two months at 55° C.

Example 5

Immunochromatographic Test for Malaria

Non-sugar organic-compatible solutes were used to stabilize antibody on nitrocellulose and gold. A concentration of 0.1% polyhistidine was able to stabilize the aldolase recombinant. A sample stored at 30° C. was shown to have stability for a minimum of 29 days when it was previously stable for only 2 days.

Example 6

Combination of 2% w/v of Ecotine L-histadine, Taurine and L-Threonine Confers Stability to Conjugate Pad Drying Buffer W/O Sucrose A 5× conjugate drying buffer was prepared following the SOP formulation except that the SOP 25% w/v sucrose was excluded. A combination of control, anti *P. falciparum* and anti *P. vivax* gold particles were adjusted to 1× by addition of 5× drying buffer and brought to 2% w/v each of ecotine L-histidine, taurine and L-threonine. SOP conjugate pad matrix was striped, dried and stored in desiccated vials at both 4° C. and 55° C. for 19 months and 11 days. Vials were removed to RT and allowed to equilibrate and pads from each temperature were inserted into malaria urine dipstick format devices. The same combination of recombinant *P. vivax* antigen and tissue culture supernatant *P. falciparum* antigen was run on one of each device. Equivalent sensitivity was observed for conjugate pad stored at both 4° C. and 55° C. despite the absence of sucrose in the drying pad buffer formulation.

Example 7

4% w/v of L-Histadine Alone Does Not Confer Stability to Conjugate Pad Drying Buffer W/O Sucrose 5× conjugate drying buffer was prepared following the SOP formulation except that the SOP 25% w/v sucrose was excluded. A combination of control, anti *P. falciparum* and anti *P. vivax* gold particles were adjusted to 1× by addition of 5× drying buffer and brought to 4% w/v. SOP conjugate pad matrix was striped, dried and stored in desiccated vials at both 4° C. and 55° C. for 19 months and 11 days. Vials were removed to RT and allowed to equilibrate and pads from each temperature were inserted into malaria urine dipstick format devices. The same combination of recombinant *P. vivax* antigen and tissue culture supernatant *P. falciparum* antigen was run on one of each device. Much higher sensitivity was observed for conjugate pad stored at 4° C. than for pad stored at 55° C. Additionally, a significant quantity of conjugate was retained in the conjugate pad matrix of the 55° C. material after the run.

EQUIVALENTS

Those skilled in the art will recognize, or be able to ascertain using no more than routine experimentation, many equivalents to the embodiments of the invention described herein. Such equivalents are intended to be encompassed by the following claims.

We claim:

1. A method for preserving the activity of one or more biologically active molecules in a dried and reconstituted state, comprising:
    a) depositing the one or more biologically active molecules onto a surface;
    b) depositing one or more non-sugar organic compatible solutes onto the surface, wherein said one or more non-sugar organic compatible solutes are each selected from the group consisting of: glycine, alanine, serine, proline, sodium glutamate, lysine, aminobutric acid, taurine, amines, betaine, sarcosine, trimethylamine N-oxide, 2-Naphthol, ectoine, hydroxyectoine, glycerine, deoxyribonucleic acid, adenosine monophosphate, PCR primers, spermine, spermidine, polyethyleneimine, polyhystidine, polythymadilic acid, acetyl-L-carnitine, and L-citruline; and
    c) drying the deposited one or more biologically active molecules and the deposited one or more non-sugar organic compatible solutes on the surface, wherein the one or more non-sugar organic compatible solutes preserves the activity of the one or more biologically active molecules in the dried and reconstituted state.

2. The method of claim 1, wherein the one or more biologically active molecules and the one or more non-sugar organic compatible solutes are deposited onto said surface concurrently.

3. The method of claim 2, wherein each of the one or more biologically active molecules are selected from the group consisting of: an antibody, a labeled antibody, an antibody fragment and a labeled antibody fragment, and the one or more non-sugar organic compatible solutes comprise single amino acids.

4. The method of claim 2, wherein the one or more biologically active molecules are selected from the group consisting of: an antibody, a labeled antibody, an antibody fragment and a labeled antibody fragment, and the one or more non-sugar organic compatible solutes comprise single amino acid chains of about 1 to about 10 amino acids.

5. The method of claim 3, wherein each of the one or more biologically active molecules are selected from the group consisting of: an immobilized antibody, an immobilized antibody fragment, a mobilizable labeled antibody and a mobilizable labeled antibody fragment, and the surface comprises a portion of a test strip.

6. The method of claim 5, wherein the test strip is immunochromatographic.

7. The method of claim 5, wherein the portion of the test strip is a conjugate pad.

8. The method of claim 5, wherein the portion of the test strip is a detection zone.

9. The method of claim 5, wherein said immunochromatographic strip comprises a lateral flow device.

10. The method of claim 2, wherein said one or more biologically active molecules are selected from the group consisting of: an antibody, a labeled antibody, an antibody fragment and a labeled antibody fragment, and said one or more non-sugar organic compatible solutes comprise one or more amines.

11. The method of claim 2, wherein said one or more biologically active molecules are selected from the group consisting of: an antibody, a labeled antibody, an antibody fragment and a labeled antibody fragment, and said one or more non-sugar organic compatible solutes comprise osmolytes or other compatible solutes.

12. A method for preserving the activity of one or more biologically active molecules in a dried and reconstituted state, comprising:
    a) providing a sample;
    b) providing a test strip with at least a portion comprising the one or more biologically active molecules and one or more non-sugar organic compatible solutes, wherein said one or more non-sugar organic compatible solutes protects and preserves the activity of said one or more biologically active molecules in the dried and reconstituted state, wherein said one or more non-sugar organic compatible solutes are each selected from the group consisting of: glycine, alanine, serine, proline, sodium glutamate, lysine, aminobutric acid, taurine, amines, betaine, sarcosine, trimethylamine N-oxide, 2-Naphthol, ectoine, hydroxyectoine, glycerine, deoxyribonucleic acid, adenosine monophosphate, PCR primers, spermine, spermidine, polyethyleneimine, polyhystidine, polythymadilic acid, acetyl-L-camitine, and L-citruline;

c) contacting said with said test strip; and d) detecting the presence of or measuring the amount of an analyte in the sample, wherein said one or more non-sugar organic compatible solutes protects and preserves the activity of said one or more biologically active molecules in the dried and reconstituted state.

13. The method of claim 12, wherein the portion of the test strip is a conjugate pad.

14. The method of claim 12, wherein the portion of the test strip is a detection zone.

15. The method of claim 12, wherein the test strip is immunochromatographic.

16. The method of claim 12, wherein the test strip comprises a lateral flow device.

17. A test strip defining a flow path and comprising:
a porous member comprising, in dry form:
a labeled binding reagent configured to bind an analyte, and
at least one non-sugar organic compatible solute,
a porous strip separate from and in fluid contact with the porous member, the porous strip comprising a detection zone, and
a binding reagent disposed along the flow path and configured to bind the analyte and/or a complex of the analyte and the labeled binding reagent:
wherein, the binding reagent is configured to capture the analyte and/or the complex of the analyte and the labeled binding reagent in the detection zone upon the mobilization of the labeled binding reagent by a liquid comprising the analyte, and the non-sugar organic compatible solute is selected from the group consisting of glycine, alanine, serine, proline, sodium glutamate, lysine, aminobutric acid, taurine, amines, betaine, sarcosine, trimethylamine N-oxide, 2-Naphthol, ectoine, hydroxyectoine, glycerine, deoxyribonucleic acid, adenosine monophosphate, PCR primers, spermine, spermidine, polyethyleneimine, polyhystidine, polythymadilic acid, acetyl-L-camitine, and L-citruline.

* * * * *